(12) United States Patent
Tennican et al.

(10) Patent No.: US 8,778,387 B2
(45) Date of Patent: *Jul. 15, 2014

(54) ANTIMICROBIAL MEDICAL DRESSINGS AND PROTECTING WOUNDS AND CATHETER SITES

(75) Inventors: Patrick O. Tennican, Spokane, WA (US); L. Myles Phipps, Seattle, WA (US)

(73) Assignee: Hyprotek, Inc., Spokane, WA (US)

( * ) Notice: Subject to any disclaimer, the term of this patent is extended or adjusted under 35 U.S.C. 154(b) by 194 days.

This patent is subject to a terminal disclaimer.

(21) Appl. No.: 12/874,188

(22) Filed: Sep. 1, 2010

(65) Prior Publication Data

US 2011/0052664 A1    Mar. 3, 2011

Related U.S. Application Data

(60) Provisional application No. 61/239,130, filed on Sep. 2, 2009.

(51) Int. Cl.
*A61L 15/16* (2006.01)
(52) U.S. Cl.
USPC ............ 424/447; 424/406; 424/443; 424/446
(58) Field of Classification Search
USPC .......................... 424/400–406, 443, 446, 447
See application file for complete search history.

(56) References Cited

U.S. PATENT DOCUMENTS

| | | | |
|---|---|---|---|
| 5,438,984 A | 8/1995 | Schoendorfer | |
| 5,556,375 A | 9/1996 | Ewall | |
| 5,973,221 A | 10/1999 | Collyer et al. | |
| 6,063,029 A | 5/2000 | Saita et al. | |
| 6,168,800 B1 | 1/2001 | Dobos et al. | |
| 7,282,186 B2 | 10/2007 | Lake, Jr. et al. | |
| 2004/0037789 A1 | 2/2004 | Moneuze et al. | |
| 2004/0110841 A1 | 6/2004 | Kite et al. | |
| 2006/0142684 A1 | 6/2006 | Shanbrom | |
| 2007/0179373 A1 | 8/2007 | Pronovost | |
| 2008/0057136 A1* | 3/2008 | Polyakov et al. ............. | 424/620 |
| 2012/0288571 A1* | 11/2012 | Tennican et al. ............. | 424/616 |
| 2013/0287860 A1* | 10/2013 | Tennican et al. ............. | 424/616 |

FOREIGN PATENT DOCUMENTS

| | | |
|---|---|---|
| CN | 2546003 | 4/2003 |
| CN | 2705167 | 6/2005 |
| CN | 1711845 | 12/2005 |
| CN | 1813097 | 8/2006 |
| GB | 350384 | 6/1931 |
| WO | WO9204923 | 4/1992 |
| WO | WO2004108091 | 12/2004 |
| WO | WO2005003436 | 1/2005 |
| WO | WO2005025486 | 3/2005 |
| WO | WO 2006089139 A2 * | 8/2006 |
| WO | WO2009076718 | 6/2009 |

OTHER PUBLICATIONS

Hospenthal et al., "Guidelines for the Prevention of Infections After Combat-Related Injuries", Journal of Trauma Injury, Infection, and Critical Care, vol. 64, No. 3, Mar. 2008, pp. S211-S220.
McGee et al., "Preventing Complications of Central Venous Catheterization", The New England Journal of Medicine, vol. 348, No. 12, Mar. 20, 2003, pp. 1123-1133.
Singhal et al., "Wound Infection", eMedicine from WebMD <<http://www.emedicine,medscape.com>>, Updated Sep. 15, 2009, 32 pages.
The PCT Search Report mailed May 20, 2011 for PCT Appliction No. PCT/US10/47756, 11 pages.
Non-Final Office Action for US Patent Application mailed on Feb. 15, 2013, Patrick O. Tennican et al., "Antimicrobial Agents and Methods of Use", 12 pages.
The PCT Search Report mailed Aug. 1, 2011 for PCT application No. PCT/US11/22150.
"Versene Acid—Solubility", The Dow Chemical Company, Sep. 15, 2010, pp. 1-3.
"VERSENE NA Disodium EDTA Chelating Agent", The Dow Chemical Company, Oct. 2009, pp. 1-2.
The Australian Office Action mailed Nov. 4, 2013 for Australian patent application No. 2010289415, a counterpart foreign application of U.S. Appl. No. 12/874,188, 3 pages.
Final Office Action for U.S. Appl. No. 13/554,962, mailed on Dec. 5, 2013, Patrick O. Tennican, "Antimicrobial Agents and Methods of Use", 14 pages.
Office Action for U.S. Appl. No. 13/924,410, mailed on Nov. 22, 2013, Patrick O. Tennican, "Antimicrobial Agents and Methods of Use", 15 pages.
Translated Chinese Office Action mailed Aug. 12, 2013 for Chinese patent application No. 201080047665.8, a counterpart foreign application of U.S. Appl. No. 12/874,188, 13 pages.
Translated Chinese Office Action mailed Oct. 17, 2013 for Chinese patent application No. 201180006632.3, a counterpart foreign application of U.S. Appl. No. 13/554,962, 13 page.
Office Action for U.S. Appl. No. 13/924,410, mailed on Mar. 28, 2014, Patrick O. Tennican, "Antimicrobial Agents and Methods of Use", 18 pages.
Australian Office Action mailed Mar. 13, 2014 for Australian patent application No. 2011207398, a counterpart foreign application of U.S. Appl. No. 13/554,962, 3 pages.
Chinese Office Action mailed Apr. 10, 2014 for Chinese patent application No. 201180006632.3, a counterpart foreign application of U.S. Appl. No. 13/554,962, 19 pages.
Chinese Office Action mailed Apr. 22, 2014 for Chinese patent application No. 201080047665.8, a counterpart foreign application of U.S. Appl. No. 12/874,188, 17 pages.
European Search Report mailed Apr. 23, 2014 for European patent application No. 10814534.3, 11 pages.

* cited by examiner

*Primary Examiner* — Michael G Hartley
*Assistant Examiner* — Micah-Paul Young
(74) *Attorney, Agent, or Firm* — Lee & Hayes, PLLC

(57) ABSTRACT

An antimicrobial medical dressing provides a combination of antimicrobial agents in various concentrations that protect against microorganisms, absorb exudates, and promote healing. The antimicrobial agents may include compositions of ethanol, hydrogen peroxide, and/or ethylenediaminetetraacetic acid.

8 Claims, 4 Drawing Sheets

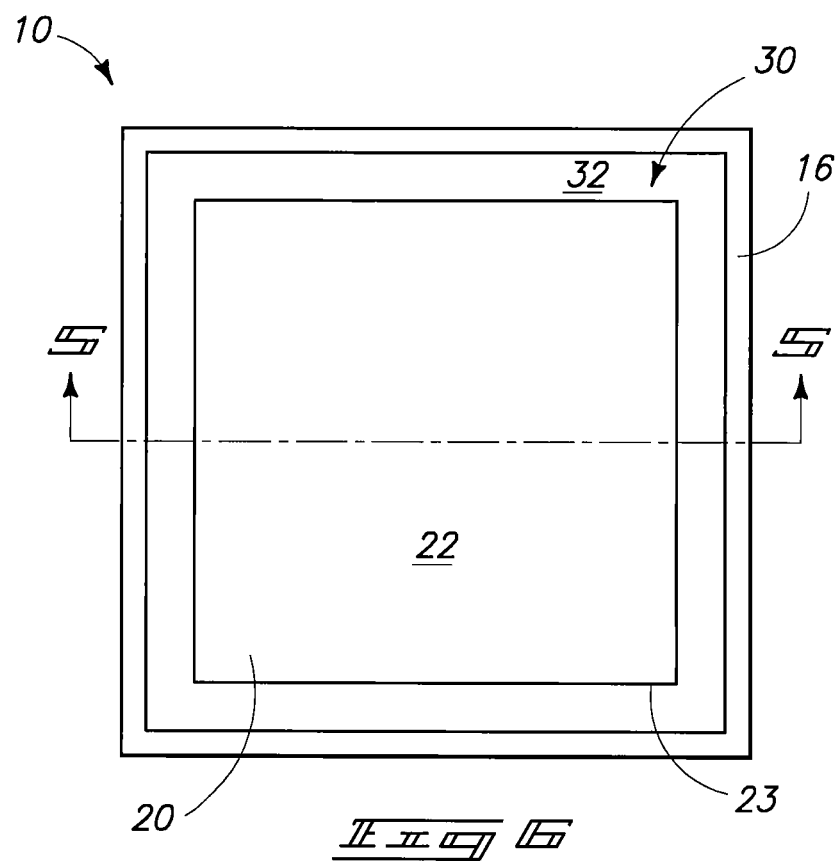
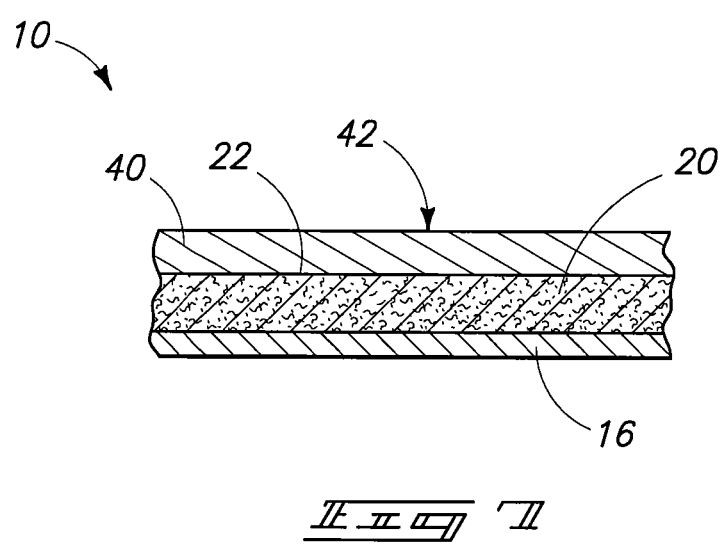

ANTIMICROBIAL MEDICAL DRESSINGS AND PROTECTING WOUNDS AND CATHETER SITES

CROSS-REFERENCE TO RELATED APPLICATION

This U.S. Nonprovisional Patent Application claims the benefit of U.S. Provisional Patent Application No. 61/239, 130, filed on 2 Sep. 2009, and entitled "Antimicrobial Medical Dressings and Methods of Protecting Wounds and Catheter Sites." U.S. Provisional Patent Application No. 61/239, 130 is hereby incorporated by reference in its entirety.

BACKGROUND

Conventional medical dressings are used for a variety of reasons, such as wound dressings, post-surgical dressings, and other specialized situations. The functions of conventional medical dressings may include protecting a wound site and protecting against microbes. In some instances, a conventional medical dressing may be used when victims experience serious traumas or war wounds in remote locations. For example, conventional medical dressings may be applied to the victims before medical attention is available, which creates a problem of trapping debris, dirt and ever-present contaminating microorganisms from the surrounding environment within the wound site. Another problem occurs when adding antimicrobial agents to conventional medical dressings. The added antimicrobial agents tend to be overly aggressive, causing tissue damage, or too mild, failing to protect against a broad spectrum of microbes. Use of the antimicrobial agents in medical dressings has presented a challenge.

In other instances, antimicrobial agents are used to prepare a surgical site. Typically, use of the antimicrobial agents includes cleansing the skin with alcohol followed by povidone iodine, or alternatively cleansing of the skin with alcohol followed by chlorhexidine. However, once prepared in this manner, the surgical site is vulnerable to recontamination via touch-borne or air borne organisms, which may lead to transmitting the organisms into a patient's surgical site, tissue, or possibly bloodstream. Thus, preventing possible bacterial contamination around the pre-surgical site has presented a challenge.

Yet another challenge with bacterial contamination occurs with catheters and drainage tubes. Catheters may allow drainage of fluids, injection of fluids, or access by surgical instruments and drainage tubes allow drainage of fluids. A problem occurs with prolonged use of the catheters or the drainage tubes, which creates a vulnerability of an infection at a point of entry (i.e., catheter site or drainage site). Skin in the immediate vicinity of a catheter site or a drainage site may be contaminated with skin bacteria, such as *pseudomonas aeruginosa, staphylococcus aureus*, and the like. The bacteria in the skin around the catheter site or the drainage site may enter a patient's bloodstream and may pose life-threatening challenges. Thus, preventing possible bacterial contamination around the catheter site or the drainage site presents another challenge.

SUMMARY

This disclosure describes protecting against microorganisms by using an infection inhibiting solution and antimicrobial agents in a medical dressing. In an implementation, the infection inhibiting solution includes a composition of hydrogen peroxide carbamide peroxide, ethylenediaminetetraacetic acid, sodium citrate, or alcohol in various concentrations.

In another implementation, a medical dressing includes a bottom layer, a gas permeable membrane layer over the bottom layer, an antiseptic disposed within the gas permeable membrane layer, and an absorbent material layer over the gas permeable membrane layer. The antiseptic includes hydrogen peroxide, carbamide peroxide, ethylenediaminetetraacetic acid, sodium citrate, or alcohol.

In yet another implementation, the disclosure describes a method of inhibiting infection at a catheter site. The method includes providing a dressing that includes an antiseptic disposed within a gas permeable membrane layer. The antiseptic includes hydrogen peroxide, ethylenediaminetetraacetic acid (EDTA), disodium EDTA, or ethanol. Also, the method describes inserting a catheter through a slit into a central opening in the dressing, and applying a front surface of the dressing to the skin of a patient.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIG. 6 illustrates a top view of the example antimicrobial medical dressing of FIG. 5.

FIG. 7 illustrates a cross sectional view of yet another example antimicrobial medical dressing.

DETAILED DESCRIPTION

Overview

An infection inhibiting solution is described in an implementation and an antimicrobial medical dressing with a combination of antimicrobial agents is described in another implementation. The infection inhibiting solution also contains antimicrobial agents. The antimicrobial agents in the solution and the combination of the antimicrobial agents in the dressing are used in various concentrations to protect against microorganisms, to absorb exudates, and/or to promote healing. The antimicrobial agents used in the infection inhibiting solution and used in the antimicrobial medical dressing may include hydrogen peroxide, carbamide peroxide, ethylenediaminetetraacetic acid, sodium citrate, or alcohol in various concentrations.

The infection inhibiting solution and the antimicrobial medical dressing both offer protection against the microorganisms to achieve different purposes. For example, various concentrations of the antimicrobial agents may be provided to protect against the microorganisms at the different stages of trauma or stages of healing. For instance, the antimicrobial medical dressing may be applied initially for traumas such as war wounds, burns, cuts, scrapes, and the like. The antimicrobial agents in the antimicrobial medical dressing may be applied in stepwise reduction to adjust to the antimicrobial needs of a patient at different stages of healing.

As another example, antimicrobial or infection inhibiting agents may provide protection against contamination by microorganisms during use of catheters and drainage tubes. In particular, the antimicrobial medical dressing may be placed at a catheter site to provide protection against microorganisms at the catheter site, intended for extended indwelling. The antimicrobial medical dressing reduces or eliminates a near-site contamination of the microorganisms and reduces or eliminates the microorganisms that form biofilms on catheter ports and lumens.

As yet another example, antimicrobial medical dressings may be used in pre-surgery and during surgery to achieve and maintain a sterile site. The antimicrobial medical dressing may provide ongoing protection against microorganisms, while providing access to a surgery site at the same time. There are many other possible uses of the antimicrobial medical dressing.

While aspects of described techniques can be implemented in any number of different medical dressings, and/or compositions, implementations are described in the context of the following illustrative antimicrobial medical dressings.

Example of Antimicrobial Medical Dressing

Antimicrobial medical dressings, methods of preventing wound infections, methods of preventing infections at catheter sites and infection inhibiting or infection preventing solutions are described herein. Example antimicrobial medical dressings are described generally with reference to FIGS. 1-9.

Figure 1:
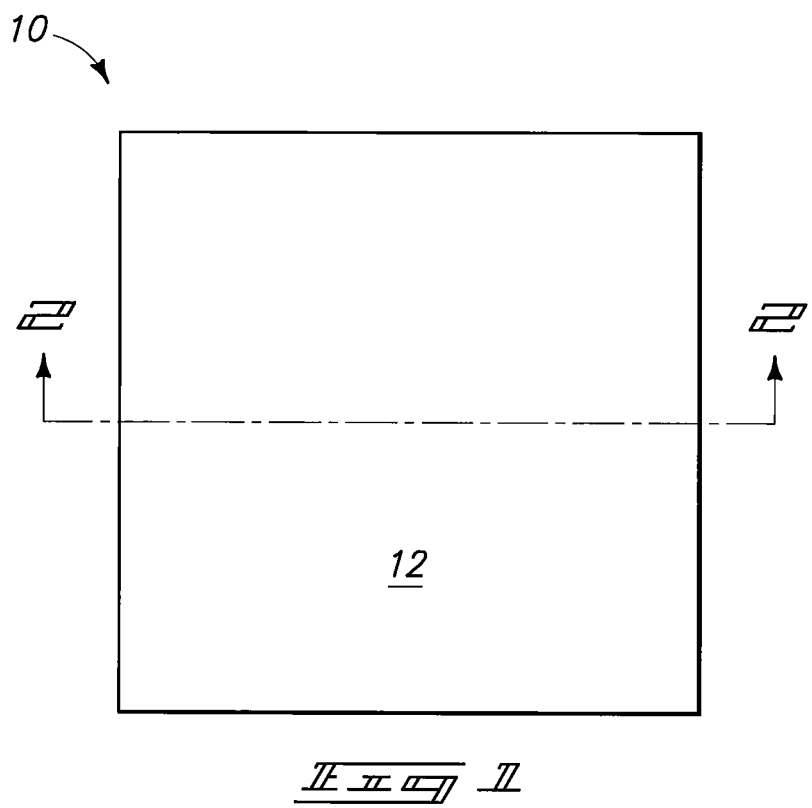
FIG. 1 illustrates a back view of an example antimicrobial medical dressing.

FIG. 1 shows a back view of an illustration of an example antimicrobial medical dressing 10. The antimicrobial medical dressing 10 includes a backside 12. The antimicrobial medical dressing 10 is shown as having a square shape, although alternative shapes are contemplated such as, for example, a round shape, a rectangular shape, an oval shape, a polygon shape, and the like.

Figure 2:
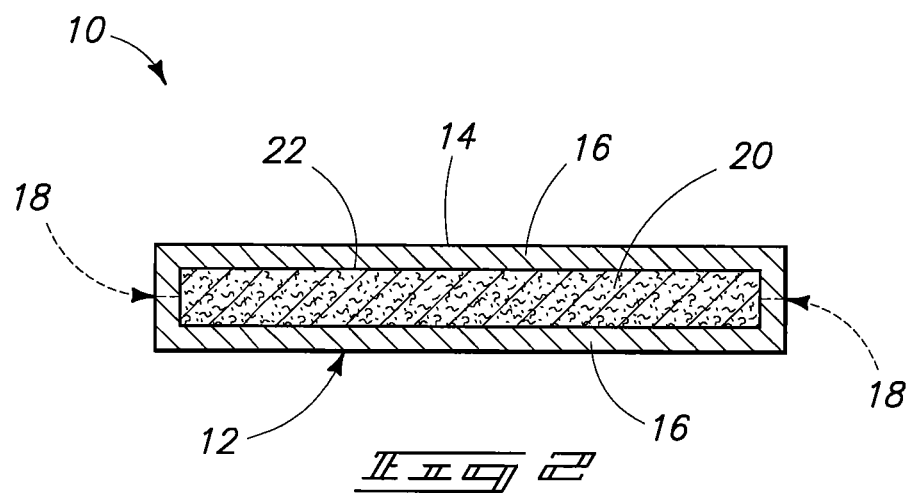
FIG. 2 illustrates a cross sectional view of the example antimicrobial medical dressing of FIG. 1.

FIG. 2 illustrates a cross sectional view of the antimicrobial medical dressing 10 shown in FIG. 1. The cross sectional view is taken along line 2-2 of FIG. 1, with the backside 12 disposed along the bottom of FIG. 2. The antimicrobial medical dressing 10, as initially provided, has an upper surface 14 opposing the backside 12.

The antimicrobial medical dressing 10 includes a backing layer 16, which may be a vapor barrier or a physical barrier layer. The backing layer 16 may additionally function as an oxygen barrier. Example materials for the backing layer 16 include, but are not limited to, polyethylene, aluminum foil, aluminum oxide, silicon oxide coated polymeric films, polypropylene, organo silicon-based polymers (silicones) polytetrafluoroethylene (Teflon), and polyvinyl chloride. Additionally, inorganic ceramic materials, generally in finely divided or powdered form, containing absorbed, microencapsulated or otherwise incorporated antimicrobial agents may be utilized to provide a controlled release of the antimicrobial agents. In implementations, the barrier layer 16 may be a bi-layer or a tri-layer of two or more combinations of these materials. As shown in FIG. 2, the backing layer 16 may be provided initially at an upper surface of the antimicrobial medical dressing 10. An upper region (above perforation lines 18) of the backing layer 16 may differ in composition from a lower region of the backing layer 16, with the upper and lower region materials being selected, for example, from the materials described above or other materials.

The antimicrobial medical dressing 10 may also include a membrane 20 disposed over the lower region of the backing layer 16, such that as initially provided, the membrane 20 is completely encased by the backing layer 16 as shown in FIG. 2. The membrane 20 is preferably composed of a polymer material, which allows diffusion of oxygen and liquid. Alternatively, the membrane 20 may be a gas permeable membrane layer. Example materials, which may be utilized for the membrane 20 include, but are not limited to, gel materials such as starch polymer, cellulosic gel, polyethylene foam, and silicone open cell foam. The membrane 20 may be infused, coated, or impregnated with a solution or a gel, which has antimicrobial properties. Such a solution or a gel may contain one or more of hydrogen peroxide, carbamide peroxide, other oxidizing agents, ethanol, ethylenediaminetetraacetic acid (EDTA, salts of EDTA, sodium citrate, other chelating agents, detergents, and water. In another implementation, the solution may include hydrogen peroxide, EDTA, ethanol, and water in various concentrations.

Figure 3:
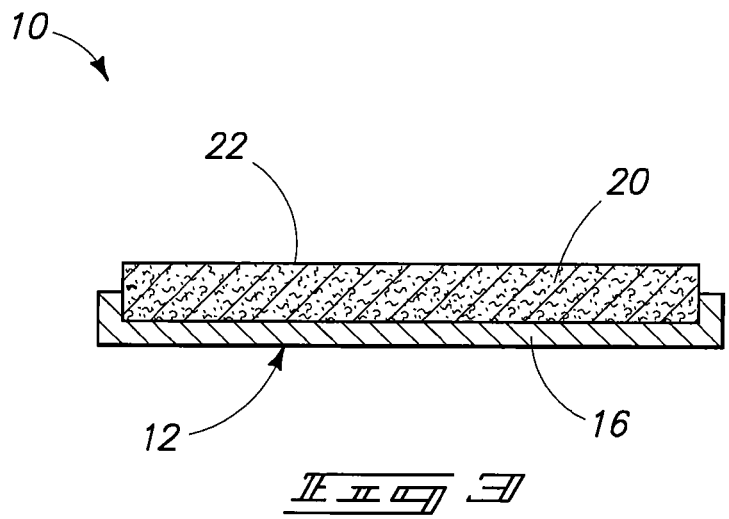
FIG. 3 illustrates a cross sectional view of another example antimicrobial medical dressing.

As shown in FIG. 2, a perforation or a score line may be provided between the upper portion and the lower portion of the backing layer 16. The perforation or the score line is provided to allow removal of the upper portion of the backing layer 16 to expose an upper surface 22 of the membrane 20 as shown in FIG. 3. Alternative methods of connecting upper and lower layers of the backing material 16 are contemplated such as, for example, adhesive, heat sealing, and the like, to join the two backing layers to maintain a vapor barrier along the site of joining.

FIG. 3 illustrates a cross sectional view of an example antimicrobial medical dressing 10. Shown is the upper surface 22 of the membrane 20, which is configured to interface with a wound site. The upper surface 22 may include a translucent, transparent, or semi-transparent material in order to provide access to a surgical site while still providing protection against microorganisms. By applying the upper surface 22 of the membrane 20 to the wound site, an infused infection inhibitory or preventive solution is brought into contact with a patient's or a person's skin allowing an infection inhibitory effect or an infection preventive effect. The terms "infection inhibition solution" may be used interchangeably with the terms "infection prevention solution" to indicate solutions that contain the antimicrobial agents in various concentrations that protect against microorganisms, absorb exudates, and/or promote healing.

Antimicrobial medical dressings may be utilized for wounds that disrupt, puncture, or pierce the skin. Exemplary wound types include, but are not limited to, punctures, burns, cuts, and abrasions. In addition, the antimicrobial medical dressings may be utilized for medical procedures that require inserting a device into a patient's body. Exemplary types of medical procedures include surgical incisions, needle sites, catheter sites (e.g., intravascular or urinary dialysis catheter), peritoneal dialysis sites, laparoscopic surgery access sites, intravascular line ports, drainage tube sites, and the like. Furthermore, the antimicrobial medical dressings may be utilized for pretreatment of sites where a medical procedure will occur. For example, a needle site, incision site or a catheter site may be identified and an antimicrobial medical dressing may be applied prior to performing the medical procedure. Such site preparation may pre-treat the site with the antimicrobial infection inhibiting solution to prevent or to minimize risks of infection occurring during the medical procedure. A protective dressing with the antimicrobial agents may be left in place until the surgical procedures is performed. An additional protective dressing may be applied post procedure to further minimize risks of infection. Additionally, the use of a chelating agent in the antimicrobial solution within the membrane 20 may inhibit matrix metalloproteinase (MMP) activity. Binding of the divalent cofactor, zinc, reduces destructive catalyzed hyperinflammatory reactions.

The presence of chelating agents may be useful in treating burns. The inhibitory effect on metalloproteinases or metalloproteases (either or both, MMPs) may decrease or avoid further tissue destruction, which may be caused by an increased level of the MMPs. In the case of burns, unfettered MMP activity may increase a severity of the burn, by depth and area. Accordingly, treatment of burns with the antimicrobial medical dressings or infection prevention solutions that contain appropriate chelating agents in proper concentrations may decrease or prevent the potential tissue destruction caused by the MMPs. The appropriate chelating agents may include but are not limited to citrate, EDTA or its salts, other substituted compounds, such as salicylic acid or salicylate esters and many others known to those familiar with the art. The concentrations tend to be in a range as chelators vary in strength, stability, and other variables. Wound conditions also vary considerably. In practice, the concentrations may be based on observations of healing progress or lack thereof.

Antimicrobial agents have many purposes. For instance, microbicidal refers to agents that kill an organism (e.g., sporicidal, virucidial, bactericidal, and protozoacidal). Microbistatic refers to agents that inhibit growth of an organism (e.g., bacteriostatic, fungistatic, and sporistatic). Another purpose is destruction of microbial defense mechanisms. For example, the destruction of microbial defense mechanisms protects systemically administered antimicrobials for wound infections or surgical prophylaxis. A molecule such as aminoglycoside (i.e., gentamicin, tobramycin, and amikacin) may allow therapeutic levels of a drug to act against bacteria. This may be particularly important for bacteria that are highly resistant gram negative rod (i.e., *Pseudomonas* species (ssp), *Acinetobacter* ssp, and *Escherichia coli* ssp). The antimicrobial agents described above may inactivate an organisms' enzymes (i.e., phosphorlylases, aminoacetyl transferases) thereby preserving an activity of the aminoglycoside against the bacteria. For example, some of the biochemical mechanisms for the anti-defense systems are known, beta lactam (penicillin-like), cephalosporin, and carbapenem antibiotics.

Figure 4:
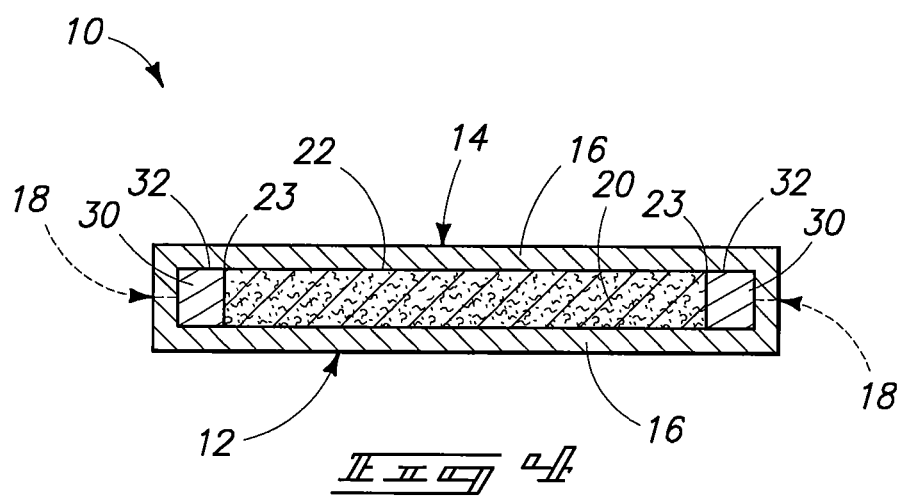
FIG. 4 illustrates a cross sectional view of another example antimicrobial medical dressing.

FIG. 4 illustrates a cross sectional view of an antimicrobial medical dressing 10 in accordance with an alternative aspect of the antimicrobial medical dressing. The embodiment shown in FIG. 4 contains all of the elements of the embodiment of FIG. 2, and such features are numbered identically to the earlier figures. Additional features are assigned new identifiers. In this embodiment, the membrane 20 has outer most edges 23. In the embodiment shown, an adhesive material 30 is provided in a peripheral region of the antimicrobial medical dressing 10 beyond the outer most edges 23 of the membrane 20.

Figure 5:
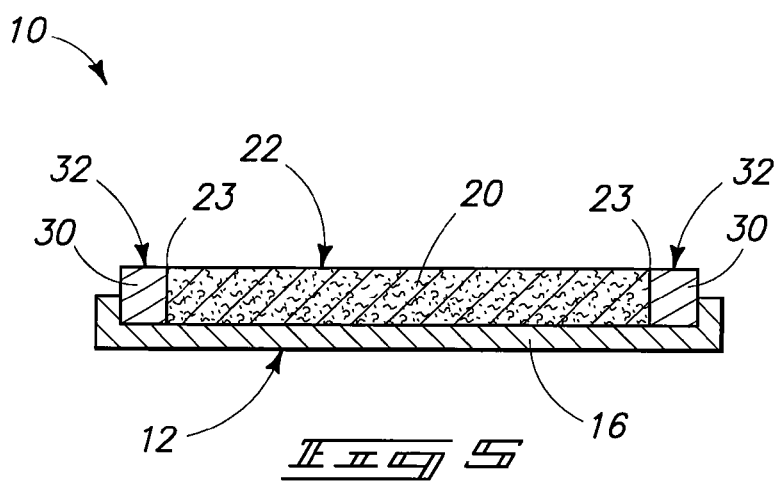
FIG. 5 illustrates a cross sectional view of still another example antimicrobial medical dressing.

FIG. 5 illustrates a cross sectional view of still another example antimicrobial medical dressing 10. The adhesive material 30 has an uppermost surface 32, which may be exposed by removal of an upper layer of the backing later 16 as shown in FIG. 5. The uppermost surface 32 is configured to interface with a patient's skin in a region outside the wound site.

FIG. 6 illustrates a top view of an example antimicrobial medical dressing 10 shown in FIG. 5. The cross sectional view shown in FIG. 5 has been taken along line 5-5 of FIG. 6. As shown in FIG. 6, the adhesive material 30 may be provided around an entire perimeter region of the antimicrobial medical dressing 10. Alternatively, the adhesive material 30 may be provided intermittently around the periphery, along fewer than all the sides, at the corners only of the perimeter, etc. (not shown).

The size of the antimicrobial medical dressing 10 is not limited to any particular size. The antimicrobial medical dressing 10 may be provided in a variety of sizes, with or without adhesive. The antimicrobial medical dressing 10 may be provided as small as a size of an area to cover a single needle puncture site or as large as a size of an area to cover large bodily burns.

FIG. 7 illustrates a cross sectional view of another example antimicrobial medical dressing 10. The structures identified earlier are assigned the same numerical identifier and additional features are assigned new numeric identifiers. As shown, an additional layer 40 is composed of material that may be provided over the upper surface 22 of the membrane 20. In this aspect, an outermost surface 42 is configured for interfacing with a patient's skin. The outermost surface 42 is preferably an absorbent material, which is sponge like and may be a felt type or cellulosic material. The presence of such material may be beneficial for absorbing fluids away from the skin such as sweat, blood or wound seepage.

Figure 8:
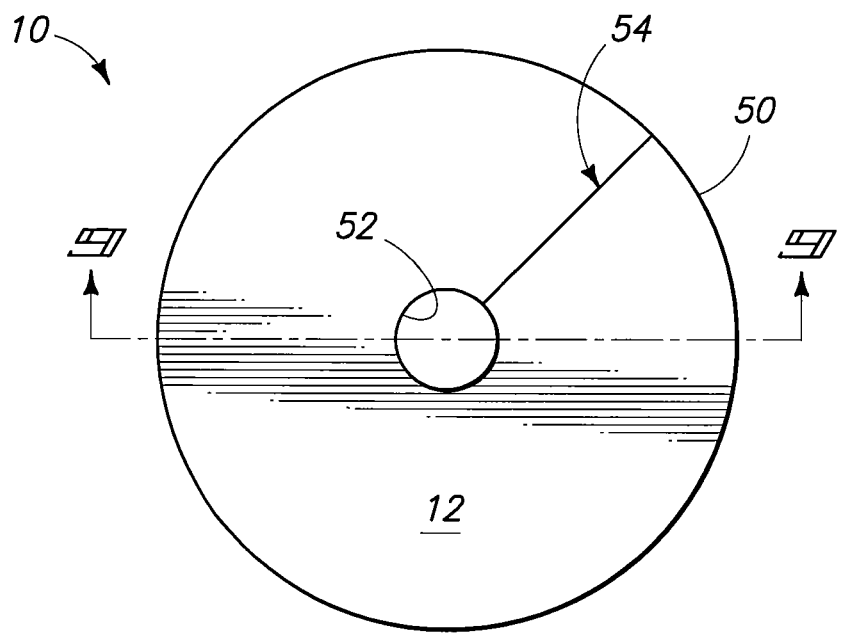
FIG. 8 illustrates a back view of an example antimicrobial medical dressing for placement at a catheter site.
Figure 9:
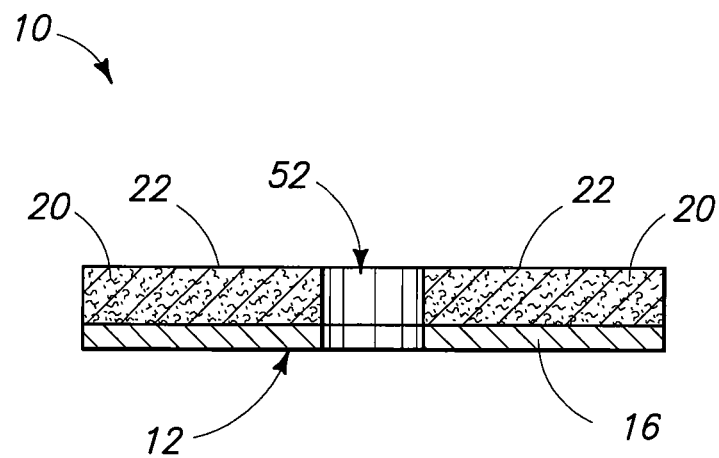
FIG. 9 illustrates a cross sectional view of the example antimicrobial medical dressing of FIG. 8.

FIGS. 8 and 9 illustrate an example antimicrobial medical dressing configured for placement at a catheter site. FIG. 8 illustrates a back view of an antimicrobial medical dressing 10. The antimicrobial medical dressing 10 is shown as being circular in shape, although alternative shapes are contemplated. For example, the alternative shapes that may be included, but are not limited to an oval shape, a rectangle shape, a square shape, a polygon shape, and shapes designed to fit specific body parts. Additionally alternative shapes are anticipated which are not generally planar but are three-dimensional, i.e., convex, concave or some combination thereof to provide a good fit to specific body parts, for example to treat head wounds, elbow wounds and the like. The antimicrobial medical dressing 10 includes an outer edge 50. A central opening 52 may be located in a center that passes entirely through the antimicrobial medical dressing 10. A slit 54 may be provided which extends from the central opening 52 to the outer edge 50 of the antimicrobial medical dressing 10. The slit 54 passes through all layers of the antimicrobial medical dressing 10.

FIG. 9 illustrates a cross sectional view of the example antimicrobial medical dressing of FIG. 8. The cross sectional view in FIG. 9 is taken along line 9-9 of FIG. 8. As shown in FIG. 9, the central opening 52 also extends through all layers of the membrane 20. The antimicrobial medical dressing 10 of this embodiment may be applied at a catheter site by positioning a catheter through the central opening 52 via the slit 54 and placing the upper surface 22 against the patient's skin. The membrane 20 may be infused, impregnated, or coated with a solution or a gel containing antimicrobial agents. The solution may contain one or more of hydrogen peroxide, carbamide peroxide, other oxidizing agents, ethanol, EDTA, sodium citrate, other chelating agents, detergents, benzyl peroxide, and water. In another implementation, the solutions or compositions in a gel form may include hydrogen peroxide, EDTA, ethanol, and water in various concentrations. It is to be noted that any or all of the optional features described such as adhesive and optional absorbent layer may be utilized in conjunction with the features shown. The size of the antimicrobial medical dressing shown in FIGS. 8 and 9 is not limited to any particular size; however, some implementations may utilize a 2 to 3 inch diameter for the antimicrobial medical dressing for catheter applications.

In some implementations, the antimicrobial medical dressing may be configured to have a slit, a hole, a tab, or other opening. The opening may be positioned over an area of skin where a device is to be inserted to a patient, such as an injection site, a catheter site, an incision site, a donor skin graft site, and the like. The antimicrobial medical dressing may remain in place during the medical procedures with the procedure performed through the opening. This allows the site to remain as sterile as possible since a minimum of tissue is exposed to the environment during the medical procedure.

Prior to use, the antimicrobial medical dressings described from FIGS. 1-9 may be contained in an outer protective packaging. The outer protective packaging may include, but is not limited to, a pouch, a sleeve, and/or a wrapper, which are sterilized. Sterilization of the antimicrobial medical dressing in the outer protective packaging may occur by gamma irradiation, electron beam irradiation, vaporized hydrogen peroxide, or other conventional methods of sterilization.

Examples of Applications of Infection Inhibiting Solutions

The antimicrobial medical dressing additionally includes infection inhibiting solutions for use in cleansing wound sites, intravascular line ports, and the like. For example, the infection inhibiting solutions may be infused, impregnated, or coated in the membrane 20 of the antimicrobial medical dressing 10. In general, the infection inhibiting solutions comprise water, ethylenediaminetetraacetic acid (EDTA), ethanol, and hydrogen peroxide at different concentrations. The infection inhibiting solutions may comprise water (i.e., $H_2O$), a strong and non-toxic chelator such as EDTA, a short-chain monohydric alcohol (e.g., ethanol with a molecular formula of $C_2H_5OH$ and an empirical formula of $C_2H_6O$), and a strong, small molecule oxidizing agent such as hydrogen peroxide (i.e., $H_2O_2$). In particular aspects, the solutions may preferably consist essentially of water, EDTA, ethanol, and hydrogen peroxide.

The antimicrobial agents may be in a liquid form, such as the solution or in a gel form, either of which includes at least two chemical species. The two or more chemical species may be compatible with each other (i.e., no adverse reactions occur on mixing) and preferably are not significantly reactive with each other, with the exception that a pH adjusting agent may be needed, i.e., hydrogen peroxide. The combination of the chemical species may be able to form a stable suspension or preferably a stable solution. The antimicrobial agents may be miscible or at least moderately soluble in aqueous media or pure water. Also, the chemical species in the antimicrobial agent may each separately and aggregately be non-toxic to humans at concentrations, which may be employed in the antimicrobial agent. Additionally, the chemical species in the solution may include small molecule compounds, thus facilitating ready diffusion across the semi-permeable membrane of the dressing. Also, at least one of the chemical species may have a buffering action to allow the pH of the solution to be adjusted to the desired final pH, and to maintain the pH for a period of time that is sufficient for the dressing to perform its full functions. Generally, the desired pH is that of the body's physiological value, approximately about 7.4, but other pH values might be more desirable in specific or unusual cases. Furthermore, the chemical species in the antimicrobial agent have differing degrees of lipophillic and lipophobic properties, thus allowing the antimicrobial agent to be "engineered" to specific solvent characteristics, depending on the needs of a specific application. For example, alcohol in a near-pure or concentrated form, as a candidate for inclusion in the antimicrobial solution, is highly lipophillic. Yet, alcohol is also lipophobic when present in smaller concentrations in water.

The solutions with the antimicrobial agents typically contain less than or equal to approximately 70% ethanol, by volume, and preferably less than or equal to approximately 50% ethanol, by volume. In yet another implementation, the solutions may contain ethanol in a range of approximately 5% to approximately 30%. The solutions additionally contain approximately 5 to approximately 50 mg/ml of ethylenediaminetetraacetic acid (EDTA) or its salts, such as Na, K, Ca, or disodium EDTA. The solutions may contain less than or equal to approximately 7.5% hydrogen peroxide, by volume. In another implementation, the solutions may contain approximately 0.5% hydrogen peroxide to approximately 5% hydrogen peroxide. The remaining volume of the solution is composed of water.

For some applications, high concentrations of alcohol, 40% or higher, are needed. In such applications, the EDTA concentration should be as high as possible. However, EDTA is almost insoluble in ethanol. Thus, two highly desirable characteristics of the antimicrobial agent, high ethanol concentration and high EDTA concentration, cannot be prepared in a simple and stable solution. However, during experimentation, an unexpected result occurred in the presence of hydrogen peroxide. The precipitation of solid EDTA is avoided, even in the high ethanol solution concentrations that are used in the antimicrobial agents described here. The range of potential antimicrobial agent concentrations increased significantly. Thus, the functional value of the hydrogen peroxide is extended from providing antimicrobial properties to providing a means of preparing solutions high in both ethanol and EDTA. In an implementation, the solution includes concentrations of about 1.5% to about 6% for hydrogen peroxide, up to about 20 mg/mL of EDTA, up to about 70% of ethanol, and the remaining volume of the solution is composed of water. The hydrogen peroxide content of the solution, added prior to the addition of the ethanol, stabilizes the solution that includes a combination of hydrogen peroxide, EDTA, and water. The EDTA remains in the solution at significantly higher levels than is possible with a combination of ethanol, water, and EDTA, when the pH is in the near-neutral range.

In an implementation, the solution includes EDTA and ethanol each in mutual concentrations that are in amounts that are not stable and with hydrogen peroxide. In yet another implementation, the solution includes these acts: adding a dry amount of EDTA to a vessel; adding an amount of about 20% to about 30% hydrogen peroxide; adding a minimal amount of water; adding a dilute amount about 0.1 to about 1.0 M NaOH, while stirring in a presence of a pH electrode, wherein the stirring is continued until the pH reaches a minimal value and remains steady for approximately one minute; adding an amount of ethanol to reach a desired percentage while stirring and monitoring the pH; adding more NaOH to reach a desired pH value; and adding more water to bring the infection inhibiting solution to desired concentrations. The acts may be performed in any order and with a variety of agents.

The infection inhibiting solutions of the invention may be utilized for medical procedures, such as to pre-treat needle injection sites, catheter sites, or incision sites. Methodology includes identifying the needle injection sites, catheter sites, or incision sites and applying the infection inhibiting solution to the skin at the identified sites. The solutions may further be utilized for cleansing, such sites post procedure.

The infection inhibiting solution may also be used as an antiseptic in the antimicrobial medical dressing for a variety of reasons. It may be used for an initial wound treatment, and as healing progresses, the need for an aggressive antimicrobial agent in the dressing may still present but to a smaller degree because of the decreased microbial load. A desirable feature of the antimicrobial medical dressing may be an ability to adjust concentrations, amounts, or compositions to meet the antimicrobial needs of the patient at a current stage of healing. A stepwise reduction of antimicrobial power may be released based on the concentrations, amounts, or compositions. In particular, the healing tissue has biochemical needs, such as normal chemical signaling and nutrient needs, growth factors and the like that vary depending on a stage of healing. Aggressive antimicrobial therapy at later stages in healing process may be detrimental by interfering with reparative, enzymatic, and histochemical mechanisms. Thus, releasing higher concentrations of the antimicrobial agents in the infection inhibiting solutions initially, and gradual stepwise reduction of the antimicrobial power based on each stage of healing is useful in some cases. Simply lowering the overall concentration of the antimicrobial agent may be sufficient in some cases. In other implementations, altering the composition of the antimicrobial agent by lowering the relative concentration of one or more components while leaving the others unchanged might be more efficatious.

In an implementation, the infection inhibiting solution is used an antiseptic in the antimicrobial medical dressing. The composition may include EDTA, ethanol, water, and hydrogen peroxide. EDTA at concentrations described above has an ability to inactivate the bacterial enzymes that are capable of destroying hydrogen peroxide. The bacterial enzymes include catalase, superoxide dismutase, and glutathione reductase. EDTA has the ability to chelate metallic ions (i.e., $Fe+2$, $Zn+2$) for enzymatic activity. EDTA inhibits similar enzymes in blood or serum, thereby prolonging activity of hydrogen peroxide on skin and soft tissue. This augments a delayed release antimicrobial and antibiofilm effect.

In another implementation, the antimicrobial medical dressing may be applied to a surgical area prior to the beginning of the surgical procedure, creating, and maintaining an uncontaminated skin zone while simultaneously allowing surgical entry and visibility. The antimicrobial medical dressing may establish the uncontaminated zone by antimicrobial action. This, in turn, could be more effective than current practice because it could be applied at a sufficient time before the surgical procedure to allow the antimicrobial action to work more thoroughly. Penetration of skin and tissue layers deeper is possible with the antimicrobial medical dressing than it would be possible by using a simple topical application of a very strong antimicrobial before starting the incision. The antimicrobial medical dressing may be structured in such a manner as to allow the surgical procedure to proceed while the antimicrobial medical dressing remains in place over the site, while simultaneously allowing surgical access. For these reasons, having the layer nearest the skin (i.e., proximal to the patient's skin) made of a translucent or semi-transparent, elastic material is beneficial. Also, the material is semi-permeable, allowing the transfer of small molecule agents from an absorbent reservoir, such as the membrane described in the drawings, containing the antimicrobial agents, layered within the distal part of the antimicrobial medical dressing. This transfer provides a continuous and controlled supply of the antimicrobial agents into the site.

In yet another implementation, the antimicrobial medical dressing may include a partial opening to allow visual observation of the progress of the site while maintaining the site and the surrounding skin in a protected state. Also, after visual observation of the site, the antimicrobial medical dressing may be readily returned to its protective functions, minimizing dressing changes with their accompanying risks, while maintaining dressing patency. Preferably, this observation, then, may be done without disturbing the proximal semipermeable layer, but would require reversibly folding back the most distal durable protective layers, most probably simultaneously and reversibly folding back the absorbent layers.

In another implementation, the infection inhibiting solutions may be combined into a gel material for various applications. The gel material may include but is not limited to a polyol or other inert gel material. The gel may be utilized prior to performing a medical procedure to prepare a wound site, post procedure, around a catheter site, an incision site, and the like. Application of the infection inhibiting solutions and gels may be further be utilized in applications of swabs or polymeric foam applications. In yet another implementation, the infection inhibiting solutions and gels may be utilized in applications of hand cleansers in gel or foam.

Next, is a discussion of applying the infection inhibiting solutions to inhibit, reduce, or prevent the growth of bacteria. The skin in the immediate vicinity of the catheter entry point (i.e., the "site") is generally contaminated with common skin bacteria. Many of these common microbial agents are rarely harmful on intact skin but pose serious, even life-threatening challenges if entered into a patient's deep tissue or even into the bloodstream. The microorganisms may include *Staphylococcus aureus* and vancomycin-resistant enterococci. The microorganisms are also capable of forming protective biofilms on available surfaces, such as polymeric surfaces of medical devices that may include catheter ports and lumens, and in some recently discovered cases, the wound tissue itself. The microorganisms form biofilms that are even more protective of the microorganisms therein, and significantly reduce their sensitivity to antimicrobial agents. Biofilms are an aggregate of microorganisms that may adhere to surfaces and protect themselves by producing a resistant "slime" layer consisting primarily of exopolysaccharide and a number of other components generally including proteins, endotoxins from dead bacteria, DNA, fibrous materials, and even host proteins.

As discussed above, the infection inhibiting solutions containing the antimicrobial agents described herein are used in the antimicrobial medical dressings. In particular, there are several applications of the antimicrobial medical dressing with the infection inhibiting solution placed at the catheter site. The terms "antimicrobial medical dressing with the infection inhibiting solution placed at the catheter site" may be used interchangeably with the terms "antimicrobial medical dressing for the catheter site" to indicate the dressing with the solution that is placed at the catheter site.

The antimicrobial medical dressing for the catheter site reduces or eliminates the near-site contamination of microbes and particularly those capable of forming biofilms. Also, the antimicrobial medical dressing for the catheter site creates an uncontaminated zone of skin near a catheter site. This zone could be kept in an uncontaminated state for at least 1-3 days without requiring a change in antimicrobial medical dressing. Furthermore, the antimicrobial medical dressing for the catheter site provides access to the catheters multiple times per day, while maintaining the uncontaminated skin zone.

Microbial systems, either in biofilms or as planktonic (free-swimming) organisms utilize a complex system of biochemical reactions to sustain their life processes. For example, biofilm-forming organisms, specifically gram negative bacteria, utilize acyl homoserine lactone (AHL) derived compounds as quorum sensing compounds. The AHL contains several fatty acid ester groups. The esters, being the product of a reaction between a carboxylic acid and an alcohol, may be subject to reactions that break the acid away from the alcohol.

The reactions may include hydrolysis, or alternatively, transesterification where the original alcohol is replaced by a new alcohol, generating a different carboxylic acid ester. Schematically:

Hydrolysis of ester: R—COOEt+$H_2$O→R—COOH+ EtOH where R represents a carboxylic acid carbon chain.

Applying this to the specific case of AHLs, shown is hydrolysis of an AHL:

AHL-COOR+$H_2$O→AHL-COOH+R—OH(a new carboxylic acid)  (equation 1)

a. Transesterification of an AHL:

b. AHL-COOR+EtOH→AHL-COOEt+HOH(water).

Either of these reactions produces a compound that is no longer suited to its original function of stimulating the production of a biofilm. The probability of the formation of a biofilm is thus reduced.

Turning to a discussion of an endotoxin, a toxin that is a structural molecule of the bacteria. Two commonly known are lipopolysaccharides (LPSs) and lipooligosaccharides (LOSs), which are released by the death of gram-negative bacteria and the dissolution of their cell walls. The endotoxins are extremely toxic, able to cause severe disease, for example toxic shock or death in adults at microgram levels or less. The endotoxins are composed of lipid (fatty acids, predominantly), polysaccharide chains, and usually some protein material. The bonds that connect the polysaccharide to the fatty acid portion are esters, where the sugar-moiety provides the alcohol function.

Both regular hydrolysis and transesterification reactions may happen to LPSs, and in either case, the products are of very little or no toxicity and are broken down to simpler molecules by ordinary metabolic processes.

LPS hydrolysis: LPS+H2O→L—H+PS—OH

Lipid polysaccharide

LPS ethanolysis: LPS+EtOH→L-OEt+PS—H

Lipid ester polysaccharide

Either of these reactions breaks down the substance. Thus, the infection inhibiting solutions are used to reduce the potential dangerous effects of releasing endotoxins.

The effects of EDTA (e.g., chelation) in the infection inhibiting solutions may prevent microorganism growth in several ways: EDTA chelation itself may be represented by the following schematic, where Ca+2 is the divalent calcium ion and the EDTA is in the dianionic state, EDTA-2:

Chelation: EDTA-2+Ca+2→EDTA-Ca(the EDTA-monocalcium complex)

It has been shown that *staphylococcus epidermidis* bacterial concentration may be lowered by EDTA, only slightly less than that amount due to vancomycin. In other instances, EDTA's ability to chelate metal ions may block biofilm formation, thereby freeing the indwelling bacteria. Thus, the indwelling bacteria become susceptible to killing by the ethanol and the hydrogen peroxide that are in the infection inhibiting solution.

It is also known that EDTA chelates iron ions. For example, iron ions (Fe+2 and Fe+3) are ubiquitous requirements for bacterial and fungal growth. EDTA readily chelates both ionic forms. It follows that the addition of EDTA, which chelates Fe, removes Fe from the growth medium, also prevents bacterial and fungal growth, which would otherwise occur. The chelation of iron follows:

Chelation of iron (Fe+2) ions:

Fe+2-chloride+EDTA→Fe+2-EDTA complex+chloride-2

No Bacterial or Fungal Growth

As mentioned above, some species of bacterial and fungal microbes have the ability to form spores, which are highly protective of the organism itself. However, the ability of the organism to form spores greatly exacerbates the problem of destroying the spores as they form a very resistant spore coat. It has been shown that such spore-formers require divalent manganese ion, Mn+2 as part of the sporulation process. EDTA is known to be able to chelate the divalent Mn+2 ion, thus removing it from the solution and retarding or completely preventing the formation of spores. The process follows:

Mn+2+EDTA→Mn+2-EDTA complex

No Bacterial or Fungal Sporulation

It is also known that EDTA has an additional benefit, which may be speculated to be related to chelation. This additional effect is that the presence of EDTA, bacterial spores are unable to convert to a vegetative state. Electron microscopic examination of these spores in the presence of EDTA is unable to detect ultrastructural damage. The spores in the presence of EDTA appear identical in all respects to normal spores, but are unable to germinate, thereby rendering them non-viable.

As discussed above, the infection inhibiting solutions are used in the antimicrobial medical dressings. In particular, there are several applications of the antimicrobial medical dressing with the infection inhibiting solution. The antimicrobial medical dressing with the infection inhibiting solution reduces or prevents microorganisms from forming before surgery, during surgery, after surgery, and during healing at the various stages. Furthermore, the antimicrobial medical dressing with the infection inhibiting solution removes dead or old tissue from wounds in order to promote healing.

When injured tissue is healing, one of the imperatives is that old, diseased, or even dead tissue should be removed. In order to accomplish this task, the healing body utilizes a number of agents, in particular enzymatic materials to break down cellular components. One such class of enzymes, proteinases, is commonly found. Among the proteinases are the matrix metalloproteinases (MMPs). MMPs contain a metallic ion, usually Zn+2 at the core of the active portion of the molecule. It has been shown that the Zn+2 ion is held in the active position, but must be partially exposed for its function. MMPs are considered vital for healing, but can be overproduced and thus overreact to the healing process. EDTA may assist in controlling the overreaction, by chelation of the protruding Zn+2 ion's exposed portion:

Chelation of a Zn-ion in a MMP:

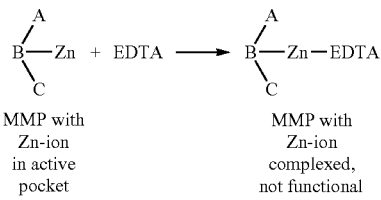

MMP with Zn-ion in active pocket    MMP with Zn-ion complexed, not functional

The antimicrobial agents, as specified in the infection inhibiting solution, have vital functions in wound healing that are not limited to those of destroying or attenuating microbial growth. Because of the ubiquitous nature of the shared biochemical properties of most of the biosphere, the antimicrobial agents may also interact with chemical species present in the wound (i.e., from the microbial viewpoint, a host). For this reason, the antimicrobial agents as specified in the infection inhibiting solution, also may act as a topical agent to modify the larger field of overall biochemical action. For example, during normal wound healing, cytokines and/or chemokines are brought into the healing area. However, overproduction of the cytokines and/or chemokines can be deleterious. Interactions of the cytokines and/or chemokines with hydrogen peroxide, by itself or in combination with ethanol and the chelator may react to change the structural make-up of the cytokine and/or the chemokine. For example, by inactivating the cytokine and/or the chemokine, their concentrations are reduced to more efficacious levels.

The antimicrobial agent, hydrogen peroxide, as specified in the infection inhibiting solution, has additional functions that are not limited to those of destroying or attenuating microbial growth. A number of biochemical bonds are formed by atoms in a reduced state, i.e., containing a minimal content of oxygen. Hydrogen peroxide or chemical radicals derived from hydrogen peroxide may often add oxygen atoms to the reduced molecules, changing their chemical structures and chemical properties. In many cases, the oxidized molecules are unable to perform normal functions, and bacterial death occurs. Many protein molecules have complex 3-dimensional shapes, which are stabilized by the presence of (—S—S—) groups. The individual S-atoms arise from cysteine amino acid residues located at locations in the protein's amino acid chain that are remote from each other, but which are able to join together, because folding, twisting or other distortion of the chain brings them into close proximity. Joining the S's together to become the —S—S— group preserves that folded or twisted feature in the structural 3-D shape of the protein. The specific shape, then is generally an absolute feature of the protein molecule that allows it to perform its enzymatic (catalytic) function. A small amount of oxidation, by hydrogen peroxide, allows major changes in the essential 3-D shape, and renders the enzyme non-functional. This may be illustrated schematically, using the symbol ABC and DEF as chains of amino acids held together by chemical bonds (bonds are represented by short vertical or horizontal lines):

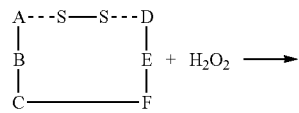

Complex folded 3-D shape of enzyme.

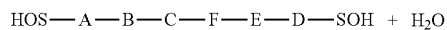

Less complex, unfolded shape, enzyme dysfunctional

The less complex shape may be further modified to higher oxidation states of sulfur such as —SOH or —SO$_2$H in some cases. Having lost the critical shape, the enzyme will no longer be able to catalyze its reactions, and bacterial death will likely occur.

Hydrogen peroxide is also known to act as a sterilant in vapor form and is commonly utilized in a number of commercially available sterilizer devices. Hydrogen peroxide used in the sterilizer devices has excellent penetrating power into the bodies of microbes and kills by a variety of mechanisms including but not being limited to the above. It is also known that liquid hydrogen peroxide has powerful antimicrobial action in higher concentrations, 7.5% or greater. However, these concentrations are not suitable for human use, because 7.5% or greater may cause caustic attack on exposed skin. Higher concentrations tend to destabilize other compounds in the antimicrobial solutions, and because the stabilization requires the solution to be highly acidic, typically below pH 3.0 and even near 2.0.

The infection inhibiting solution provides stable solutions at or near physiological pH, for example approximately pH 7.4. In implementations, the pH may range from approximately about 6.8 to approximately about 7.8 Skin applications and even applications to epithelial tissue, including cervical, vaginal, anal, and oral tissues become efficacious.

In many cases, the molecular structure includes functional groups that provide chemical "weak links" i.e. places (functional groups) where the molecule is subject to lysis by the agents in the antimicrobial mixture. Often, when those functional groups are broken apart into their simpler components, the newly released components have the potential to reform into the original linkage thus regenerating the original molecule and its properties. This is counterproductive to the overall healing process. For example, cleavage of an ester by hydrolysis generates two smaller molecules, an alcohol, and a carboxylic acid. These are able to rejoin by reversing in some circumstances into the ester:

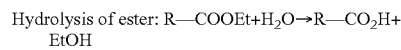

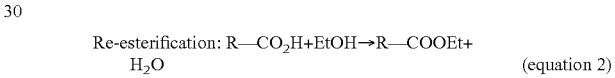

(equation 2)

A more specific example is the AHLs where the R-groups are long chain fatty acids and the alcohol are generally sugar molecules as shown in equation 1. Sugars contain several oxygen-based functional groups and in some cases other groups, which are capable of being oxidized. It would be desirable to prevent the reverse reaction shown above as equation 2 in which the hydrolysis products reverse. The reverse reaction reforms the functional AHL, and allows quorum sensing and biofilm formation to proceed. Hydrogen peroxide may modify the structure of oxidizable sites in molecules via several routes. For example, by attaching —OH groups on the sugar, if the structural features allow, can become ketonic or aldehydic groups. In either case, the hydrogen peroxide may prevent reaction reversibility (equation 2) by modification of the original reaction products. Thus even if re-esterification does occur, the product of that reaction cannot be a normal AHL, and therefore could not function to carry biofilm signals.

Oxidation of a sugar to a ketonic product (SuA and SuB=Sugar moieties) may be shown by:

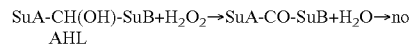

A Ketonic Sugar Derivative

Oxidization of a Sugar to an Aldehydic Product:

An Aldehydic Sugar Derivative

Tissue hypoxia is highly undesirable during wound healing. Some wound pathogens, that may include anaerobic bacteria or *Clostridium perfringens*, are only able to grow in an environment of low oxygen tension. As a result of ischemia and tissue hypoxia, severe or even catastrophic gas gangrene can result in limb loss or death. The infection inhibiting solution is highly oxidative, mainly because of the hydrogen peroxide content. Because of its small molecule nature, and its particular molecular solubility in aqueous media and ability to cross cellular barriers with the assistance of ethanol, the hydrogen peroxide creates an environment within the wound area that is highly oxygenated. Such an oxygenated environment, in either wet or dry conditions is positively stimulating to wound healing in general, avoiding the negative effects of ischemia.

Tissue hypoxia also causes impairment of the phagocytic function of host white blood cells. The hydrogen peroxide creates an oxygen-rich environment that promotes the restoration of normal phagocytic function in host white blood cells and augments the normal bactericidal action of phagocytes.

CONCLUSION

Although the subject matter has been described in language specific to structural features and/or compositions, it is to be understood that the subject matter defined in the appended claims is not necessarily limited to the specific features or compositions described. Rather, the specific features and compositions are disclosed as illustrative forms of implementing the claims.

We claim:

1. An infection inhibiting composition consisting of a solution of:
    approximately 5 to approximately 50 mg/ml of a chelator;
    less than or equal to approximately 70% ethanol, by volume;
    less than or equal to approximately 7.5% hydrogen peroxide, by volume; and
    water.

2. The composition of claim 1, wherein said hydrogen peroxide is present in an amount of less than or equal to approximately 3%, by volume.

3. The composition of claim 1, wherein the chelator and ethanol are both present at concentrations that are not stable in solution together absent hydrogen peroxide.

4. An infection inhibiting composition consisting of:
    approximately 5 to approximately 50 mg/ml of a chelator;
    less than or equal to approximately 70% ethanol, by volume;
    less than or equal to approximately 7.5% hydrogen peroxide, by volume;
    a pH adjusting agent; and
    water.

5. The composition of claim 1, wherein the chelator is ethylenediaminetetraacetic acid (EDTA), a salt of EDTA, sodium citrate, or combinations thereof.

6. A method of inhibiting wound infection comprising:
    identifying a wound site; and
    applying an antimicrobial dressing to the wound site, the antimicrobial dressing comprising:
        a bottom layer including a vapor barrier, the bottom layer comprising at least one or more of aluminum foil, aluminum oxide, silicon oxide coated polymeric film, polyethylene, polypropylene, polysilicone, polyvinyl chloride, polytetrafluoroethylene, or mylar;
        a gas permeable membrane layer over the bottom layer;
        The composition according to claim disposed within the gas permeable membrane layer; and
        an absorbent material layer over the gas permeable membrane layer, the absorbent material layer having an upper surface configured to interface with a patient's skin.

7. The method of claim 6, wherein the wound site is a site to be incised or a site where a catheter is to be placed and wherein the identifying and the applying are performed prior to incising or placement of the catheter to pretreat the wound site.

8. The method of claim 7, further comprising providing access through the antimicrobial dressing through the wound site to perform a surgical procedure while providing protection against microorganisms.

* * * * *